United States Patent [19]

Nakatsu et al.

[11] Patent Number: 5,240,962
[45] Date of Patent: Aug. 31, 1993

[54] ANTIOBESITY AND FAT-REDUCING AGENTS

[75] Inventors: Tetsuo Nakatsu, Walnut Creek; Zhengqing Chen, Concord, both of Calif.

[73] Assignees: Takasago Institute for Interdisciplinary Science, Inc., Walnut Creek, Calif.; Takasago International Corporation, Tokyo, Japan

[21] Appl. No.: 685,285

[22] Filed: Apr. 15, 1991

[51] Int. Cl.[5] ............................................. A61K 31/19
[52] U.S. Cl. .................................................... 514/570
[58] Field of Search ........................................ 514/570

[56] References Cited

FOREIGN PATENT DOCUMENTS 64-34913  2/1989  Japan .
2-104530  4/1990  Japan .

OTHER PUBLICATIONS

I. Kubo, et al., "Mulluscicides from the Cashew *Anacardium occidentale* and Their Large-Scale Isolation," J. Agric. Food Chem. 1986, 34, 970–973.

I. Kubo, et al., "Prostaglandin Synthetase Inhibitors from the African Medicinal Plant *Ozoroa mucronate*," Chem. Letters, 1987, 1101.

J. M. Sarkar et al., "Immobilization of beta-D-Glucosidase and beta-D-Glucosidase-Polyphenolic Complexes," Biotechnology Letters, 1983, 5; 619–624.

Primary Examiner—Frederick E. Waddell
Assistant Examiner—F. Tsung
Attorney, Agent, or Firm—Spensley Horn Jubas & Lubitz

[57] ABSTRACT

An antiobesity and fat-reducing composition and method of treating obesity in an animal, including human, in need of such treatment as well as a feed composition for an animal which employs certain naturally occurring alkyl or alkenyl phenols having 15 to 17 carbon atoms in the alkyl or alkenyl group.

14 Claims, No Drawings

ANTIOBESITY AND FAT-REDUCING AGENTS

BACKGROUND OF THE INVENTION

1. Field of the Invention

This invention relates to the use of certain naturally occurring alkyl or alkenyl phenols or their pharmaceutically acceptable base salts as antiobesity and fat-reducing agents. More particularly, it relates to a method of treating obesity in an animal, including human, by administering to the animal the foregoing alkyl or alkenyl phenols or their pharmaceutically acceptable base salts as well as to compositions containing the same which achieve the treatment of obesity.

Further, this invention relates to a method of reducing fat in an animal, including human, by administering to the animal the foregoing alkyl or alkenyl phenols or their pharmaceutically acceptable base salts as well as to compositions containing the same which achieve the reduction of fat.

2. Related Art

Obesity is the most prevalent, chronic, medical condition in our society and is directly or indirectly associated with a vast number of diseases including hypertension, diabetes, cardiovascular disease, gallstones, etc., as well as a diminished self-image with consequent psychological maladjustment in society. As such, obesity often leads to health hazards and shortened life expectancy.

The treatment of obesity remains an important and largely unachieved goal in medical science, and increased efforts to develop useful therapeutics are urgently needed The dilemma in the treatment of obesity is the pathological elevation of body weight which is mounted by the body's physiologic systems. When one system is perturbed, there is often a compensatory reaction which minimizes or negates the initial effect. Also, pharmacotherapy of obesity is at a very early stage compared with drug modalities available for treatment of other chronic diseases. Considerable progress, however, is being made in the quest of new therapeutics for the treatment of obesity which rely on one of the following pharmacologic approaches: (a) reduction of energy intake; (b) regulation of lipid and carbohydrate metabolism; and (c) enhancement of energy expenditure.

Compared with the (a) and (c) approaches, the (b) approach, which interferes with lipid or carbohydrate metabolism in the body, has not been fully exploited. One method to effectively modulate the lipid or carbohydrate metabolism is to suppress intestinal absorption of dietary lipids and/or carbohydrates. Inhibitors of intestinal lipases or glucosidases decrease the rate of the degradation of carbohydrates and triglycerides to absorbable monosaccharides and fatty acids, thereby normalizing body fat levels in obese animals.

Acarbose, is a pseudo-oligosaccharide of microbial origin and is known to competitively inhibit the action of several α-glucosidases within the gastrointestinal tract [W. Puls et al., Front. Horm. Res. 2, 235 (1980)]. Despite its potency in inhibition, symptoms of carbohydrate malabsorption and the resulting diarrhea have consistently been reported when acarbose is administered at high doses [R. Vargas et al., Clin. Pharmacol. Ther. 33, 216 (1983)]. Therefore, a search continues to find improved inhibitors of intestinal glucosidases and other carbohydrate digestive enzymes.

In veterinary areas, treatment of obese livestock or poultry has not traditionally been considered an important task compared with the treatment of obese humans. However, obesity in domestic pet animals arouses concern among pet owners who care for the animals' health and appearance. Furthermore, it has long been realized that reduction of fat content in broiler chickens, pigs and cattle is economically significant in view of increasing demand for lean meat.

Repartitioning agents such as cimaterol, ractopamine and porcine somatotropin are known to decrease fat deposition, increase lean tissue deposition, and improve efficiency of feed utilization. These agents are believed to alter the manner in which dietary energy intake is partitioned between lean and fat tissue in growing animals, thus favorably shifting the lean-fat ratio in poultry, cattle, sheep and swine. However, many of these agents are ineffective or cause adverse reactions, which limit their use. Where one of these agents may fail in an individual case, another may succeed. Thus, a continuing need for improved fat-reducing agents, which may be safe to animals and effective, is clearly evident.

Subsequent to this invention, there has been a report that a number of naturally occurring alkyl or alkenyl salicylic acids are thermogenic when tested in rat brown adipose tissue and may have a potential use as antiobesity agents (see Japan Kokai No. 2-104,530 to Okamoto et al., published April 17, 1990). However, there are no known reports concerning the inhibition of carbohydrate digestive enzymes such as intestinal α-glucosidase by the same salicyclic acids prior to the time of our invention. Nor are there any known reports concerning the use of those salicylic acids as a fat-reducing agent in human beings as well as in animals.

SUMMARY OF THE INVENTION

It has now been discovered that certain naturally occurring alkyl or alkenyl phenols or pharmaceutically acceptable base salts thereof, when administered to an obese animal, including human, produces a therapeutic benefit in regulating body weight in the animal.

It has also been discovered that the same alkyl or alkenyl phenols or pharmaceutically acceptable base salts thereof can effectively function as antiobesity agents by inhibiting the activity of some intestinal carbohydrate digestive enzymes.

It has been further discovered that the same alkyl or alkenyl phenols or pharmaceutically acceptable base salts thereof significantly reduce fat in experimental animals.

The inhibition of carbohydrate digestive enzymes as well as fat-reducing activity is observed with alkyl or alkenyl phenols of formula (I):

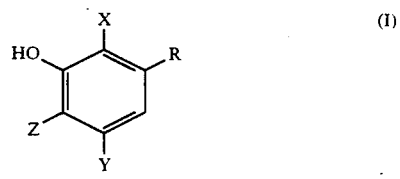

wherein R is alkyl having from 15 to 17 carbon atoms or alkenyl having from 15 to 17 carbon atoms; X is hydrogen or carboxyl; Y is hydrogen or hydroxyl; and Z is hydrogen or alkyl having from 1 to 4 carbon atoms.

Also useful in this invention are pharmaceutically acceptable base salts of the compounds of the formula (I).

This invention further provides a method of treating obesity in an animal, which comprises administering to the animal, including human, an obesity treating amount of a compound of the formula (I) or a pharmaceutically acceptable base salt thereof.

Additionally claimed is a method of inhibiting the action of intestinal carbohydrate digestive enzymes in an animal, including human, which comprises administering to the mammalian subject an enzyme inhibiting amount of a compound of the formula (I), or a pharmaceutically acceptable base salt thereof.

Also provided in this invention are: a method of reducing fat in an animal, including human, by means of the compound of the formula (I) or a pharmaceutically acceptable salt thereof; and a feed composition for cattle, sheep, swine or poultry which incorporates the compound of the formula (I) or a physiologically acceptable salt thereof into a feed ration.

DETAILED DESCRIPTION OF THE INVENTION

The compounds of the formula (I) are known and described in I. Kubo, et al., J. Argric. Food Chem. 34, 970-973 (1986). These compounds are found in certain plant species and can be isolated in quantities from cashew (*Anacardium occidentale*) nut shells. Kubo, et al. reports the detailed isolation procedure, the disclosure of which is herein incorporated by reference. The utility of compounds of the formula (I) wherein X is carboxyl, Y and Z are both hydrogen, and R is pentadecyl or 10(Z)-pentadecenyl as a prostaglandin synthetase inhibitor is also disclosed in I. Kubo, et al., Chem. Letters 1101, 1987. The anticancer activities of compounds of the formula (I) wherein X is carboxyl, Y and Z are both hydrogen, and R is $C_{15}$-$C_{17}$ alkyl or $C_{15}$-$C_{17}$ alkenyl, are found in Japan Kokai No. 64-34,913 to Nishino, et al.

A preferred group of compounds of the formula (I), because of their greater effectiveness relative to that of other compounds of the formula (I), are those wherein X, Y and Z are each hydrogen.

A second preferred group of compounds of the formula (I) are those wherein X is carboxyl; and Y and Z are each hydrogen.

A third preferred group of compounds of the formula (I) are those wherein X is hydrogen; Y is hydroxyl; and Z is alkyl having from 1 to 4 carbon atoms. Within this preferred group, Z is more preferably methyl.

A fourth preferred group of compounds of the formula (I) are those wherein X and Z are each hydrogen; and Y is hydroxyl.

Within each preferred group, particularly preferred subgroup of compounds are those wherein R is an alkyl of 15 carbon atoms or an alkenyl of 15 carbon atoms which may contain up to three double bonds in the alkenyl group. Especially preferred values for the R substituent in the formula (I) are 8(Z), 11(Z), 14-pentadecatrienyl; 8(Z), 11(Z)-pentadecadienyl; 8(Z)-pentadecenyl; and pentadecyl.

The pharmaceutically (or physiologically) acceptable base salts of the compounds of the formula (I) are those formed from bases which form non-toxic base salts. These particular non-toxic base salts include, but are not limited to; sodium, potassium, calcium, and magnesium. These salts can easily be prepared by simply treating the acidic compounds of the formula (I) with an aqueous solution of the desired cation, and then evaporating the resulting solution to dryness while preferably being placed under reduced pressure.

Alternatively, they may also be prepared by mixing lower alkanolic solutions of the acidic compounds and the desired alkali metal alkoxide together, and then evaporating the resulting solution to dryness in the same manner as before. In either case, stoichiometric quantities of reagents are preferably employed in order to ensure completeness of reaction and maximum yields of the desired pharmaceutically (or physiologically) acceptable base salts.

In the treatment of obesity or the inhibition of intestinal carbohydrate digestive enzymes in an animal, including human, the compounds of formula (I) can be administered via the oral or parenteral routes. However, it is generally preferred to administer these compounds orally as their pharmaceutically acceptable base salts. In general, these compounds are most desirably administered in doses ranging from about 10 mg up to about 1 g per day, although variations will still necessarily occur depending upon the weight of the animal being treated. However, a dosage level that is in the range of from about 1 mg to about 50 mg per kg of body weight per day is most desirably employed in order to achieve effective results, with a preferred oral range in human of about 2.0-30 mg/kg. Other variations may also occur in this respect, depending upon the species of the animal being treated and its individual response to the medicament, the particular type of pharmaceutical formulation chosen, and the time period and interval at which such administration is carried out. In some instances, dosage levels below the lower limit of the aforesaid range may be more than adequate, while in other cases still larger doses may be employed without causing any harmful or deleterious side effects to occur provided that such higher dose levels are first divided into several smaller doses that are to be administered throughout the day.

For purposes of oral administration, tablets containing various excipients such as sodium citrate, calcium carbonate and dicalcium phosphate may be employed along with various disintegrants such as starch and preferably potato or tapioca starch, alginic acid and certain complex silicates, together with binding agents such as polyvinylpyrrolidone, sucrose, gelatin and acacia. Additionally, lubricating agents such as magnesium stearate, sodium lauryl sulfate and talc are often very useful for tableting purposes. Solid compositions of a similar type may be employed as fillers in soft elastic and hard-filled gelatin capsules; preferred materials in this connection also include lactose or milk sugar as well as high molecular weight polyethylene glycols. When aqueous suspensions and/or elixirs are desired for oral administration, the essential active ingredient may be combined with various sweetening or flavoring agents, coloring matter or dyes and, if so desired, emulsifying and/or suspending agents, together with such diluents as water, ethanol, propylene glycol, glycerin and various combinations thereof.

Although the preferred mode of administration of the compounds of the formula (I) or their pharmaceutically acceptable salts is oral, they may be administered parenterally as well.

For purposes of parenteral administration, solutions of these particular compounds in sesame or peanut oil or in aqueous propylene glycol may be employed, as well as sterile aqueous solutions of the corresponding water-soluble base salts previously enumerated. Such aqueous solutions should be suitably buffered if necessary and the liquid diluent rendered isotonic with sufficient saline or glucose. These particular aqueous solutions are especially suitable for intravenous, intramuscular and subcutaneous injection purposes. In this connection, the sterile aqueous media employed are readily obtained by standard techniques well known to those skilled in the art. For instance, distilled water is ordinarily used as the liquid diluent and the final preparation is passed through a suitable bacterial filter, such as a sintered-glass filter, or a diatomaceous-earth or unglazed porcelain filter.

In the treatment of fat reduction in an animal including human, the administration of the compound of formula (I) or its route is not significantly different from those hereinbefore detailed.

When contemplating the use of the compound of formula (I) or a physiologically acceptable salt thereof as a fat-reducing agent in non-human animals (such as cattle, sheep, poultry and swine), it is convenient to administer the compound by mixing it into the animal's feed. In this case, the compound of formula (I) will be added to the animal's feed at a level which will provide the appropriate daily dosage of the compound of formula (I). Concentrations of the active ingredient in the feed to achieve the desired dosage amount will be in the range of about 1 ppm to about 1000 ppm based on the total weight of the feed. Such admixtures with the feed are readily prepared by thoroughly mixing a suitable amount of the active compound with the solid feed, for example grains such as corn, sorghum, wheat, barley, oats and the like, soya meal, fish meal, etc., together with, if desired, other optional additives conventionally employed in the art, for example trace minerals and vitamins. If desired, the active compound may be incorporated in a concentrate or premix which is then combined with the animal feed to provide the desired dosage amount.

While it is preferred to administer the compound of the formula (I) in the feed of the animals as described above, it will be understood that other methods of oral administration may also be employed. For example, the compound may be administered in a pharmaceutically acceptable veterinary preparation such as a bolus, powder, solution, paste, syrup, or the like. Such veterinary preparation is formed by combination with the active compound in an amount sufficient to give the desired dosage amount and a pharmaceutically acceptable solid or liquid diluent or carrier.

Furthermore, the compounds of the formula (I) may be used in a form such as the crude extract from cashew nut shells. In this particular case, the crude form may be incorporated in feed compositions at the desired potency concentrations.

The therapeutic value of the compounds of the formula (I) in treating obesity or reducing fat deposition is reflected by appropriate standard biological or pharmacological tests. In one test, the ability of the test compound to inhibit the enzyme activity of carbohydrate digestive α-glucosidase or invertase is assessed. In another test, the ability of the test compound to control the body weight of an experimental animal is determined. In a further test, the ability of the test compound to reduce fat deposition in an experimental animal is determined. Typical experimental protocols, by which the above tests were conducted, are found in the following examples.

The method of this invention, and composition for accomplishing the method, can be conducted with the use of more than one compound of the formula (I) such as a mixture of several preferred compounds. However, in the following examples, only one particular compound was tested for its activity in each run.

The following examples are provided for the purpose of further illustration. Accordingly, it should be understood that the invention is not limited to the specific details of these examples.

Proton nuclear magnetic resonance spectra (NMR) were measured at 500 MHz for solutions in deuterochloroform ($CDCl_3$) and peaks are expressed in parts per million (ppm) downfield from tetramethylsilane. The peak shapes are denoted as follows: s, singlet; d, doublet; t, triplet; m, multiplet; b, broad.

PREPARATION 1

6 - Pentadecylsalicylic Acid

The title compound was prepared according to the method of Kubo [I. Kubo, et al., Chem. Letters, 1101, 1987]. A sample of the product obtained had a melting point of 90°–91° C. and spectrascopic characteristics which are identical with those of the authentic sample.

PREPARATION 2

3 - Pentadecylphenol

A mixture of unsaturated cardanols was isolated from cashew shell oil by following the procedure described in I. Kobu, et al., J. Agric. Food Chem., 34, 971 (1986). Catalytic hydrogenation of the mixture over Pd/C (5%) in methanol gave the title compound, which had the following spectroscopic characteristics: NMR ($CDCl_3$): 7.12 (t, 1H), 6.74 (d, 1H), 6.64 (s, 1H), 6.62 (m, 1H), 2.54 (m, 2H), 2.00 (bs, 2H), 1.2–1.3 (bs, 22H), 0.88 (t, 3H); ms m/e (relative intensity) 304 (M+, 12), 108 ($C_7H_7O$+H, 100).

PREPARATION 3

5- Pentadecylresorcinol

The title compound was prepared in a similar manner as described in Preparation 2 using a mixture of unsaturated cardols (isolated from cashew shell oil). The title compound had the following spectroscopic characteristics: NMR ($CDCl_3$): 6.22 (s, 2H), 6.14 (s, 1H), 4.62 (bs, 1H, OH), 2.46 (t, 2H), 1.53 (bs, 4H), 1.2–1.3 (bs, 22H) 0.86 (t, 3H); ms m/e (relative intensity) 320 (M+, 10), 124 ($C_7H_7O$,+H, 100).

PREPARATION 4

2-Methyl-5-pentadecylresorcinol

The title compound was prepared in a similar manner as described in Preparation 2 using a mixture of unsaturated methylcardols (isolated from cashew shell oil). The title compound had the following spectroscopic characteristics: NMR ($CDCl_3$): 6.21 (s, 2H), 4.62 (s, 2H, OH), 2.42 (m, 2H), 1.53 (bs, 4H), 1.2–1.3 (bs, 22H), 0.84 (t, 3H); ms m/e (relative intensity) 334 (M+, 12), 138 ($C_8H_{10}O_2$, 100).

PREPARATIONS 5–16

The following compounds were isolated from cashew nut oil substantially according to the method of I.

Kubo, et al., as described in J. Agric, Food Chem., 34, 970-973 (1986):

6-[8(z)-pentadecenyl]salicylic acid, 6-[8(z), 11(z)-pentadecadienyl] salicylic acid, 6-[8(z), 11(z), 14pentadecatrienyl] salicylic acid, 3-[8(z)-pentadecenyl] phenol, 3-[8(z), 11(z)-pentadecadienyl] phenol, 3-[8(z), 11(z), 14-pentadecatrienyl]phenol, 2-methyl-5-[8(z)-pentadecenyl] resorcinol, 2-methyl-5-[8(z), 11(z)-pentadecadienyl] resorcinol, 2-methyl-5-[8(z), 11(z), 14-pentadecatrienyl]resorcinol, 5-[8(z)-pentadecenyl] resorcinol, 5-[8(z), 11(z)-pentadecadienyl]resorcinol, and 5-[8(z), 11(z), 14-pentadecatrienyl]resorcinol.

EXAMPLE 1

α-Glucosidase Inhibition

The following phenols were tested for their ability to inhibit α-glucosidase enzyme activity.

| Compound | R | X | Y | Z |
|---|---|---|---|---|
| 1 | Pentadecyl | COOH | H | H |
| 2 | 8(Z)-Pentadecenyl | COOH | H | H |
| 3 | 8(Z), 11(Z)-Pentadecadienyl | COOH | H | H |
| 4 | 8(Z), 11(Z), 14-Pentadecatrienyl | COOH | H | H |
| 5 | Pentadecyl | H | H | H |
| 6 | 8(Z)-Pentadecenyl | H | H | H |
| 7 | 8(Z), 11(Z)-Pentadecadienyl | H | H | H |
| 8 | 8(Z), 11(Z), 14-Pentadecatrienyl | H | H | H |
| 9 | Pentadecyl | H | OH | CH$_3$ |
| 10 | 8(Z)-Pentadecenyl | H | OH | CH$_3$ |
| 11 | 8(Z), 11(Z)-Pentadecadienyl | H | OH | CH$_3$ |
| 12 | 8(Z), 11(Z), 14-Pentadecatrienyl | H | OH | CH$_3$ |
| 13 | Pentadecyl | H | OH | H |
| 14 | 8(z)-Pentadecenyl | H | OH | H |
| 15 | 8(Z), 11(Z)-Pentadecadienyl | H | OH | H |
| 16 | 8(Z), 11(Z), 14-Pentadecatrienyl | H | OH | H |

The assay was conducted essentially according to the procedure of H. L. Lai, as described in Biochem. Biophys. Res. Commun., 54, 463 (1973).

The α-glucosidase (EC3.2.1.20) was purchased from Sigma Chemical Company. The enzyme solution (100 μg/ml, 0.1 ml), 0.1 M phosphate buffer (pH 6.8, 2.55 ml), 10 mM nitrophenyl glucoside (0.1 ml), and a sample solution in DMSO (0.15 ml) were combined and incubated for 10 minutes at 37° C. After incubation, the hydrolysis was stopped by the addition of 1 ml of 16(w/v)% of sodium carbonate. Liberated p-nitrophenol was measured at 400 nm.

The results obtained with each compound are expressed below in terms of their concentrations to inhibit 50% enzyme activity.

TABLE 1

| Compound | IC$_{50}$ μg/ml |
|---|---|
| 1 | 2.5 |
| 2 | 2.2 |
| 3 | 1.3 |
| 4 | 0.3 |
| 5 | 147 |
| 6 | 90 |
| 7 | 192 |
| 8 | 68 |
| 9 | 13 |
| 10 | 55 |
| 11 | 50 |

TABLE 1-continued

| Compound | IC$_{50}$ μg/ml |
|---|---|
| 12 | 56 |
| 13 | 86 |
| 14 | 15 |
| 15 | 30 |
| 16 | 14 |

These data in Table 1 show that the compounds tested significantly inhibit the α-glucosidase activity at low concentrations and that potent inhibition is particularly observed with those in which X is carboxyl, and Y and Z are both hydrogen (anacardic acids).

EXAMPLE 2

Invertase Inhibition

The following phenols (compound numbers correspond to those designated in Example 1) were tested at a concentration of 200 μg/ml for their ability to inhibit invertase enzyme activity. The assay was conducted essentially according to the procedure of I. H. Segel, et al., as described in Biochemical Calculation, John Wiley Sons, New York, p. 287–290 (1976).

The invertase (or β-fructofuranosidase; EC 3.2.1.26) was purchased from Sigma Chemical Company. The enzyme solution (100 μg/ml, 0.1 ml), 0.2 M acetate buffer (pH 4.5, 0.2 ml), 0.5 M sucrose (0.2 ml), and a sample solution in water/DMSO (0.6 ml) were combined and incubated for 10 minutes at 37° C. After incubation, the hydrolysis was stopped by the addition of Nelson reagent. Liberated reduced sugar was measured at 500 nm by the method of Somogyi-Nelson [N. Nelson, et al., J. Biol. Chem., 153, 375 (1944)].

The results obtained with the test compounds are expressed below in terms of their inhibition of enzyme activity (%) with respect t the particular concentration level chosen.

TABLE 2

| Compound | % Inhibition |
|---|---|
| 4 | 73 |
| 8 | 55 |
| 12 | 79 |
| 16 | 32 |

These data in Table 2 show that the compounds tested significantly inhibit invertase activity.

Both α-glucosidase and invertase are known to degrade dietary carbohydrates to monosaccharrides (glucose, fructose) which can be absorbed through the gastrointestinal tract. Inhibition of these enzymes should delay or slow carbohydrate absorption from starch and sucrose and thus should decrease energy intake in the body.

EXAMPLE 3

Effect on Body Weight

Slightly obese female mice (ICR) having an average weight of 20–25 g were used in these studies. Compound 1 (Example 1; anacardic acid) was administered as a drug-food mixture. Normal mouse chow was powdered and the drug added to achieve a final concentration of 1 mg (low dose), 3 mg (intermediate dose), and 10 mg (high dose) per 100 g of food. The powdered chow was then repelleted into its usual form. Control chow was similarly prepared without addition of drug. Four groups of ten animals were assigned to receive normal chow (controls) or the drug in the low dose, in the intermediate dose or in the high dose. The animals were fed ad libitum over a 4-week period. Body weight gains were recorded daily with the results summarized in Table 3.

TABLE 3

| Group | Initial Body Weight (g) | Week One | Week Two | Week Three | Week Four |
|---|---|---|---|---|---|
| Control | 21.15 | +0.69 | +2.44 | +4.63 | +5.25 |
| Low Dose | 20.52 | +0.63 | +2.19 | +4.63 | +5.13 |
| Intermediate Dose | 21.70 | +0.56 | +2.13 | +4.5 | +5.00 |
| High Dose | 21.05 | +0.31 | +1.88 | +4.13 | +4.75 |

Data are the mean of ten animals.

Mice in all the groups gained weight throughout the experiment, but the final body weights of the two drug-treated groups were different from that of the control group. Mice in the high dose group gained less weight than mice in the control group, so did mice in the intermediate dose group. Only mice in the low dose group showed no significant deviation in body weight from the control group. Clearly, there were significant treatment effects on the body weight change of mice in the drug-treated groups.

This finding, combined with in vitro enzyme inhibiting activities, provides evidence that the naturally occurring phenols of the formula (I) have unexpected utility in treating obesity in a mammalian subject. Compound 1 showed no toxicity at a 300 mg/kg dose when administered to mice over a period of 4 weeks.

EXAMPLE 4

Effect on Fat Content of Broiler Chickens

Four groups of 5 seven-day old broiler having an average weight of 129 g were used. A test diet was available ad libitum to all birds during the test period (27 days). The diet contained the following ingredients as shown in Table 4.

TABLE 4

| Ingredient | w/w % |
|---|---|
| Ground yellow corn | 59.00 |
| Soybean meal | 19.70 |
| Fish white | 14.50 |
| Soybean oil | 4.60 |
| Calcium hydrogen-phosphate | 0.51 |
| Salt | 0.10 |
| Trace mineral and vitamin premix | 0.20 |
| DL-Methionine | 0.10 |
| TOTAL | 100.00 |

Control birds received no test compound. Two groups received different levels of compound 1 (Example 1), 1 ppm and 2 ppm, respectively. At the conclusion of the test, all birds were sacrificed and processed to determine fat weights and body weights. Feed intake was also recorded.

Results of this test are shown in Table 4.

TABLE 4

|  | Control | 0.1% | 0.2% |
|---|---|---|---|
| Fat Weight (g) | 19 | 12 | 10 |
| Final Body Weight (g) | 124 | 110 | 108 |
| Feed Consumed (g) | 2250 | 2000 | 2250 |

Data are the mean of five birds.

Birds receiving anacardic acid lost approximately 10% of the initial body weight, while significantly more decrease in fat weight was observed in the birds. This reduction in fat implies a much leaner bird.

EXAMPLE 5

Effect on Body Fat in Rats

Male Sprague-Dawley weanling rats (Bioresearch Services, Oriental Yeast Co. Ltd.) of three weeks old were used in this study. They were allotted to two treatment groups of five rats when they weighed an average of about 65 g. The animals were fed carbohydrate enriched diets ad libitum for a period of 31 days. The diet contained the following ingredients as shown in Table 6.

TABLE 6

| Ingredient | w/w % |
|---|---|
| Casein | 17.42 |
| Methionine | 0.11 |
| α-Cornstarch | 49.82 |
| Sucrose | 16.60 |
| Corn Oil | 6.00 |
| Cellulose | 4.00 |
| Vitamin Mix | 0.85 |
| Mineral Mix | 5.00 |
| Choline | 0.20 |
| TOTAL | 100.00 |

Control rate received the above diet. Two groups received different levels of compound 1 (Example 1), 0.1% and 0.2%, respectively. At the conclusion of the test, all animals were sacrificed. Inguinal fat, epididymal fat, liver, kidney, spleen, lung, heart, thymus gland, brown adipose tissue and pectoral muscle were excised and weighted.

Results of this test are summarized in Table 7.

TABLE 7

|  | DOSE | | |
|---|---|---|---|
|  | Control | 0.1% | 0.2% |
| Inguinal Fat Weight (g) | 9.1 | 7.1 | 7.5 |
| Epididymal Fat Weight (g) | 4.8 | 3.2 | 3.7 |
| Final Body Weight (g) | 324.2 | 301.6 | 311.0 |
| Feed Consumed | 515.5 | 487.6 | 500.9 |

Data are the mean of five animals.

Again, animals receiving anacardic acid lost less than 10% of their initial body weight, while significantly more decrease in fat weight was observed in the animals.

These fingers (Tables 4 and 7) show that a significant reduction of at least around 20% in fat deposition can be obtained by including anacardic acid in the animal diet. The observed fat reduction thus confirms the fat-reducing activity of the compounds of the formula (I).

EXAMPLE 6

TABLET FORMULATION

| Item | Ingredient | |
|---|---|---|
| 1 | 6-Pentadecylsalicylic acid | 250 |
| 2 | Lactose | 100 |
| 3 | Polyvinylpyrrolidone | 10 |
| 4 | Modified Starch | 10 |
| 5 | Magnesium Stearate | 3 |
|  |  | 373 mg |

1. Mix Items 1, 2 and 4 and granulate with polyvinylpyrrolidone in water or alcohol.
2. Dry the granulation at 45°.
3. Mill the dried granulation through a suitable mill.

EXAMPLE 7

TABLE: TABLET FORMULATION (Wet Granulation)

| Item | Ingredient | |
|---|---|---|
| 1 | 6-Pentadecylsalicylic acid | 250 |
| 2 | Lactose | 75 |
| 3 | Pregelatinized Starch | 15 |
| 4 | Microcrystalline Cellulose | 75 |
| 5 | Magnesium Stearate | 3 |
| | | 418 mg |

1. Mix Items 1, 2, 3 and 4 and granulate with water.
2. Dry the granulation at 50° C.
3. Pass the granulation through suitable milling equipment.
4. Add Item 5 and mix for three minutes; compress on a suitable press.

EXAMPLE 8

TABLET FORMULATION

| Item | Ingredient | |
|---|---|---|
| 1 | 6-Pentadecylsalicylic acid | 250 |
| 2 | Corn Starch (Pregelatinized) | 20 |
| 3 | Modified Starch | 10 |
| 4 | Talc | 10 |
| 5 | Magnesium Stearate | 1 |
| | | 291 mg |

1. Mix Items 1, 2 and 3 and wet granulate with water. Dry at 45° C. overnight.
2. Mill through suitable screen using appropriate milling equipment.
3. Add items 4 and 5 and mix for five minutes.
4. Fill into suitable capsule.

The invention now being fully described, it will be apparent to one of ordinary skill in the art that many changes and modifications can be made without departing from the spirit or scope of the invention.

We claim:

1. A method of treating obesity in an animal which comprises administering to the animal an obesity treating amount of a compound having the formula:

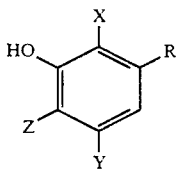

or a pharmaceutically acceptable salt thereof, wherein R is alkyl having from 15 to 17 carbon atoms or alkenyl having from 15 to 17 carbon atoms; X is hydrogen or carboxyl; Y is hydrogen or hydroxyl; and Z is hydrogen or alkyl having from one to four carbon atoms.

2. The method according to claim 1, wherein R is alkyl having 15 carbon atoms.

3. The method according to claim 1, wherein R is alkenyl having up to three double bonds.

4. The method according to claim 3, wherein R is selected from the group consisting of: 8(Z), 11(Z), 14-pentadecatrienyl; 8(Z), 11(Z)-pentadecadienyl; and 8(Z)-pentadecyl.

5. The method according to claim 1, wherein X, Y and Z are each hydrogen.

6. The method according to claim 1, wherein X is hydrogen; Y is hydroxyl; and Z is methyl.

7. The method according to claim 1, wherein X and Z are each hydrogen and Y is hydroxyl.

8. The method according to claim 1, wherein X is carboxyl and Y and Z ar each hydrogen.

9. The method according to claim 8, wherein R is alkyl having 15 carbon atoms or alkenyl having 15 carbon atoms.

10. A method of inhibiting the action of intestinal carbohydrate digestive enzymes in an animal which comprises administering to the animal an enzyme inhibiting amount of a compound having the formula:

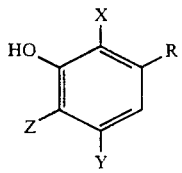

or a pharmaceutically acceptable salt thereof, wherein R is alkyl having from 15 to 17 carbon atoms or alkenyl having from 15 to 17 carbon atoms; X is hydrogen or carboxyl; Y is hydrogen or hydroxyl; and Z is hydrogen or alkyl having from one to four carbon atoms.

11. The method according to claim 10, wherein the intestinal carbohydrate digestive enzyme is α-glucosidase or invertase.

12. A method of reducing fat in an animal which comprises administering to the animal a fat-reducing amount of a compound having the formula:

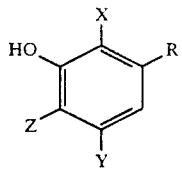

or a physiologically acceptable salt, wherein R is alkyl having from 15 to 17 carbon atoms; X is hydrogen or carboxyl; Y is hydrogen or hydroxyl; and Z is hydrogen or alkyl having from one to four carbon atoms.

13. The method according to claim 12, wherein the compound is 6-pentadecylsalicylic acid.

14. The method according to claim 13, wherein the compound is administered in the feed of the animal.

* * * * *